(12) United States Patent
Bolster et al.

(10) Patent No.: US 10,188,135 B2
(45) Date of Patent: Jan. 29, 2019

(54) METHOD FOR INDUCING SATIETY

(71) Applicants: Stokely-Van Camp, Inc., Chicago, IL (US); Glanbia Nutritionals (Ireland) Ltd., Kilkenney (IE)

(72) Inventors: Douglas Bolster, Barrington, IL (US); Laura Harkness, New Fairfield, CT (US); Brent L. Petersen, Twin Falls, ID (US); Maike Rahn, Purchase, NY (US)

(73) Assignees: Stokley-Van Camp, Inc., Chicago, IL (US); Glanbia Nutritionals (Ireland) Ltd. (IE)

( * ) Notice: Subject to any disclaimer, the term of this patent is extended or adjusted under 35 U.S.C. 154(b) by 45 days.

(21) Appl. No.: 15/071,729

(22) Filed: Mar. 16, 2016

(65) Prior Publication Data

US 2017/0119022 A1    May 4, 2017

Related U.S. Application Data

(60) Provisional application No. 62/250,996, filed on Nov. 4, 2015.

(51) Int. Cl.

| | | |
|---|---|---|
| *A23L 33/17* | (2016.01) | |
| *A23L 1/29* | (2006.01) | |
| *A23L 1/305* | (2006.01) | |
| *A21D 2/24* | (2006.01) | |
| *A23L 33/175* | (2016.01) | |
| *A23L 33/19* | (2016.01) | |
| *A21D 13/00* | (2017.01) | |
| *A23C 9/123* | (2006.01) | |
| *A23C 9/152* | (2006.01) | |
| *A23L 1/00* | (2006.01) | |
| *A23L 1/168* | (2006.01) | |
| *A23L 2/02* | (2006.01) | |
| *A23L 2/66* | (2006.01) | |
| *A23C 9/13* | (2006.01) | |

(52) U.S. Cl.
CPC .............. *A23L 33/17* (2016.08); *A21D 2/245* (2013.01); *A23L 1/293* (2013.01); *A23L 1/305* (2013.01); *A23L 1/3051* (2013.01); *A23L 33/175* (2016.08); *A23L 33/19* (2016.08); *A21D 13/00* (2013.01); *A23C 9/123* (2013.01); *A23C 9/1315* (2013.01); *A23C 9/1526* (2013.01); *A23L 1/0076* (2013.01); *A23L 1/168* (2013.01); *A23L 2/02* (2013.01); *A23L 2/66* (2013.01); *A23V 2002/00* (2013.01)

(58) Field of Classification Search
CPC ........ A23L 1/293; A23L 1/305; A23L 1/3051; A23L 1/0076; A23L 1/168; A23L 2/02; A23L 2/66; A23L 33/17; A23L 33/19; A23L 33/175; A23V 2002/00; A21D 2/245; A21D 13/00
See application file for complete search history.

(56) References Cited

U.S. PATENT DOCUMENTS

| | | |
|---|---|---|
| 7,790,670 B2 | 9/2010 | Ward et al. |
| 8,846,759 B2 | 9/2014 | Luiking et al. |
| 2011/0152184 A1 | 6/2011 | van Norren et al. |
| 2011/0233469 A1 | 9/2011 | Petersen |
| 2011/0250310 A1* | 10/2011 | Mateus .................. A23C 21/04 426/2 |
| 2012/0141445 A1 | 6/2012 | Meijer et al. |
| 2013/0210780 A1 | 8/2013 | Jourdan et al. |
| 2014/0171378 A1 | 6/2014 | Petersen et al. |
| 2014/0275283 A1 | 9/2014 | Petersen et al. |

FOREIGN PATENT DOCUMENTS

WO    WO-2013148328 A1 * 10/2013 ................ A23J 3/04

OTHER PUBLICATIONS

"A Greek Yogurt Amino Acid Profile" SF Gate dated Aug. 2, 2014, 2 pages http://healthyeating.sfgate.com/greek-yogurt-amino-acid-profile-12074.html.*
Petzke et al. Int. J. Mol. Sci. 2014, 15, 1374-1391.*
Kirchheimer, Sid "Protein diet may prompt weight loss", 3 pages, dated Feb. 7, 2003 downloaded from www.webmd.com/diet/news/20030207/protein-diet-may-prompt-weight-loss.*
Machine translation of patent CN1112367C.*
Machine Translation of CN1112367C (Year: 2003).*
Acheson et al. "Protein choices targeting thermogenesis and metabolism 1-3" Am. J. Clin. Nutr. 2011; 93:525-34 (10 pages).
Leidy et al. "Beneficial effects of a higher-protein breakfast on the appetitive, hormonal, and neural signals controlling energy intake regulation in overweight/obese, "breakfast-skipping," late-adolescent girls 1-3" Am. J. Clin. Nutr. 2013; 97:677-88 (12 pages).
Akhavan et al. "Effect of premeal consumption of whey protein and its hydrolysate on food intake and postmeal glycemia and insulin responses in your adults 1-3" Am. J. Clin. Nutr. 2010; 91:966-75 (15 pages).
Feigin et al. "Rhythmicity of plasma amino acids and relation to dietary intake 1" Am. J. Clin. Nutr. 1971; 24:329-41 (13 pages).
Leidy et al. "The role of protein in weight loss and maintenance 1-5" Am. J. Clin. Nutr. 2015; 101(Suppl):1320S-9S (10 pages).
Blundel et al. "Appetite control: methodological aspects of the evaluation of foods" 2010 International Association for the Study of Obesity 11, 251-270 (20 pages).
Batterham et al. "Critical role for peptide YY in protein-mediated satiation and body-weight regulation" Sep. 2006, Cell Metabolism 4, 223-233 (12 pages).
Cook et al. "A Scientific Review on the Effects of Whole Dairy Products, Intact Dairy Proteins, and Dairy Protein Fractions on Indicies of Satiety" Biofortis Clinical Research, Mar. 4, 2013 (77 Pages).

(Continued)

*Primary Examiner* — C. Sayala
(74) *Attorney, Agent, or Firm* — James R. Gourley; Sudhakar V. Allada; Carstens & Cahoon, LLP (57) ABSTRACT

A method for inducing satiety in a human subject is disclosed, the method providing a satiety-inducing effect by the administration of, or provision of, a food product comprising less than about 15 grams of total protein, and between about 1.0 to about 3.5 grams of total leucine. The leucine is provided by the total protein and a leucine peptide composition comprising bound leucine.

17 Claims, 7 Drawing Sheets

(56) References Cited

OTHER PUBLICATIONS

Westerterp-Plantenga et al. "Dietary protein—its role in satiety, energetics, weight loss and health" British Journal of Nutrition (2012) 108, S105-S112 (8 pages).
Soenen et al. "Proteins and satiety: implications for weight management" Current Opinion in Clinical Nutrition and Metabolic Care 2008, 11:747-751 (5 pages).
Paddon-Jones et al. "Dietary protein and muscle in older persons" Current Opinion in Clinical Nutrition and Metabolic Care 2014; 17(1):5-11 (15 pages).
Delgado, Teresa C. "Glutamate and GABA in appetite regulation" www.frontiersin.org, Aug. 2013 | vol. 4 | Article 103 (8 pages).
Ropelle et al. "A Central Role for Neuronal AMP—Activiated Protein Kinase (AMPK) and Mammalian Target of Rapamycin (mTOR) in High-Protein Diet-Induced Weight Loss" Diabetes, vol. 57, Mar. 2008; 594-605 (13 pages).
Dairy Research Institute "Higher Protein Diets and Weight Management" National Dairy Council, 2012 (8 pages).
Zhang et al. "Characterization of Peptide-YY Release in Response to Intracolonic Infusion of Amino Acids*" Endocrinology 1993, vol. 132, No. 2, 553-557 (5 pages).
Flint et al. "Reproducibility, power and validity of visual analogue scales in assessment of appetite sensations in single test meal studies" International Journal of Obesity (2000) 24, 38-48 (11 pages).
Purpera et al. "Impaired branched chain amino acid metabolism alters feeding behavior and increased orexigenic neuropeptide expression in the hypothalamus" Journal of Endocrinology (2012) 212, 85-94 (10 pages).
Smith et al. "Kinetics of Neutral Amino Acid Transport Across the Blood-Brain Barrier" Journal of Neurochemistry vol. 49, No. 5, 1987; 1651-1658 (8 pages).
Anderson et al. "Protein Source, Quantity, and Time of Consumption Determine the Effect of Proteins on Short-Term Food Intake in Young Men 1,2" Journal of Nutrition 134: 3011-3015, 2004 (5 pages).
Leidy et al. "The Influence of Higher Protein Intake and Greater Eating Frequency on Appetite Control in Overweight and Obese Men" 2010 The Obesity Society (16 pages).
Luhovyy et al. "Whey Proteins in the Regulation of Food Intake and Satiety" Journal of the American College of Nutrition, vol. 26, No. 6, 704S-712S (2007) (9 pages).
Mellinkoff et al. "Relationship Between Serum Amino Acid Concentration and Fluctuations in Appetite 1" Obesity Research, vol. 5, No. 4, Jul. 1997, 381-384 (4 pages).
Anderson et al. "Milk Proteins in the Regulation of Body Weight, Satiety, Food Intake and Glycemia" Nestle Nutr. Inst. Workshop Ser. Pediatr. Program, vol. 67, 147-159, 2011 (13 pages).
Yang et al. "Myofibrillar protein synthesis following ingestion of soy protein isolate at rest and after resistance exercise in elderly men" Nutrition & Metabolism 2012, 9:57 (9 pages).

Brouns et al. "Glycaemic index methodology" Nutrition Research Reviews (2005) 18, 145-171 (27 pages).
Pal et al. "Comparative effects of whey and casein proteins on satiety in overweight and obese individuals: a randomized controlled trial" European Journal of Clinical Nutrition (2014) 68, 980-986 (7 pages).
Pardridge, William M. "Regulation of Amino Acid Availability to Brain: Selective Control Mechanisms for Glutamate" Glutamic Acid: Advances in Biochemistry and Physiology, 1979, 125-137 (13 pages).
PreparedFoods—Sep. 2014 "NutraNews" located at http://digital.bnpmedia.com/article/NutraNews/1804915/0/article.html (1 page).
Glanbia Nutritionals, Prepared Foods, Nutra Solutions, Jun. 2012, located at www.PreparedFoods.com (1 page).
Stunkard et al. "The Three-Factor Eating Questionnaire to Measure Dietary Restraint, Disinhibition and Hunger" Journal of Psychosomatic Research, vol. 29, No. 1, 71-83 (1985) (13 pages).
Szmelcman et al. "Interference between Leucine, Isoleucine and Valine during Intestinal Absorption" Biochem. J. (1966) 100, 7-11 (5 pages).
Tang et al. "Ingestion of whey hydrolysate, casein, or soy protein isolate: effects on mixed muscle protein synthesis at rest and following resistance exercise in young men" J. Appl. Physiol. 107: 987-992, 2009 (6 pages).
Woods et al. "Regulation of Food Intake Through Hypothalamic Signaling Networks Involving mTOR" Annu. Rev. Nutr. 2008, 28:395-311 (21 pages).
Yudkoff et al. "Brain Amino Acid Requirements and Toxicity: The Example of Leucine 1,2" J. Nutr. 135: 1531S-1538S, 2005 (11 pages).
Zampieri et al. "Oral Leucine Supplementation Is Sensed by the Brain but neither Reduces Food Intake nor Induces an Anorectic Pattern of Gene Expression in the Hypothalamus" Plos One, Dec. 2013 | vol. 8 | Issue 12 | e84094 (13 pages).
ADPI—News/Statistical Information, from Nov. 2, 2015—Recent Study Shows the Prolibra Weight Management Solution Significantly Reduced Glycemic Index Units—Glanbia Nutritionals.
Frestedt et al., "A whey-protein supplement increases fat loss and spares lean muscle in obese subjects: a randomized human clinical study" Nutrition & Metabolism 2008, 5:8 (7 pages).
Hall et al., "Casein and whey exert different effects on plasma amino acid profiles, gastrointestinal hormone secretion and appetite"—British Journal of Nutrition (2003) 89, 239-248 (10 pages).
Pesta et al., "A high-protein diet for reducing body fat: mechanisms and possible caveats" Nutrition & Metabolism 2014, 11:53 (8 pages).
Brink, Will "We Are What We Absorb II: Proteins, amino acids, and peptides" Oct. 24, 2014 (3 pages).
Snarr, Chandra L. "Protein balance, metabolic and satiety responses to a leucine-rich versus isonitrogenous meal in healthy postmenopausal women" Dec. 2011 Thesis submitted to McGill University (94 pages).
Giles-Smith, Karen "Milk Proteins: Packing a Powerful Nutritional Punch"—Today's Dietitian, vol. 15, No. 3, p. 26 (6 pages).

\* cited by examiner

METHOD FOR INDUCING SATIETY

FIELD OF THE INVENTION

The present invention relates to a method for enhancing satiety using a food product. More specifically, the method described herein enhances satiety by increasing blood levels of leucine relative to a fasting level.

BACKGROUND OF THE INVENTION

Food consumption in mammals is controlled by a complex interplay between the digestive system, the central nervous system, the endocrine system, and the peripheral body. In general, the brain senses signals from the mouth, gastrointestinal tract, pancreas, and adipose tissue that reflect the body's nutritional state and uses a myriad of pathways to anticipate and adjust food intake and energy expenditure. Mammalian eating behavior is thus governed by various organoleptic factors that contribute to consumer preferences and satisfaction. Based on research to date, large protein doses (>25 g) within a single eating occasion are believed necessary to achieve a 'protein meal threshold' for the desired satiety effect (*Curr. Opin. Clin. Nutr. Metab. Care.* 2014 January; 17(1): 5-11, incorporated herein by reference). However, providing large protein doses within a single eating occasion presents organoleptic challenges when developing consumer products. Such high amounts of protein are also not cost-effective. It would therefore be beneficial to develop methods for inducing satiety that could rely on foods having lower protein levels which pose fewer formulation challenges and have improved organoleptic properties.

SUMMARY OF THE INVENTION

The present disclosure provides a method for inducing satiety in a human subject by providing to the subject a food product that can be used to deliver leucine to a consumer in such a way as to enhance blood leucine levels above those of fasting blood leucine levels, and increase satiety of the consumer while addressing palatability challenges and reducing the amount of protein necessary to induce satiety.

Below is a simplified summary of this disclosure meant to provide a basic understanding of some aspects of the products and methods described herein. This is not an exhaustive overview and is not intended to identify key or critical elements or to delineate the scope of the description. Its sole purpose is to present some concepts in a simplified form as a prelude to the more detailed description below.

The invention relates to a method for enhancing satiety by increasing blood levels of leucine relative to a fasting level, the method comprising providing to a consumer a food product, said food product comprising, per serving size, protein and leucine, said protein being present in an amount of less than about 15 grams of total protein, and said leucine being present in an amount of between about 1.0 to about 3.5 grams of total leucine, said leucine being provided by the total protein and a leucine peptide composition comprising bound leucine. In various embodiments, the satiety-inducing food or beverage product comprises between about 1.5 to about 3.0 grams of total leucine. In various embodiments, the satiety-inducing food or beverage product comprises between about 2.0 to about 3.0 grams of total leucine. In various embodiments, the satiety-inducing food or beverage product comprises between about 2.0 to about 2.5 grams of total leucine. In any of the above embodiments, the satiety-inducing food product comprises between about 8 to about 14 grams of total protein. In any of the above embodiments, the method further comprises providing the food product as part of a dietary regime.

In any of the above embodiments, the satiety-inducing food product provided to the consumer is a cereal product, a granola product, a nutritional bar, a fortified water, a fruit juice, a fruit smoothie, a dairy smoothie, a dairy beverage, an energy drink, a sachet, a shot, a baked good or a yoghurt.

In any of the above embodiments, the satiety-inducing food or beverage product induces satiety in a consumer, subject or patient in need of treatment following consumption.

In any of the above embodiments, the concentration of leucine in the blood is increased by 2-fold or more, preferably 3.5-fold or more, as compared to a fasting level of blood leucine, by providing to the consumer a food product as disclosed herein. The fasting level refers to the level of leucine in the blood of a consumer or subject after having fasted for a predetermined period of about 12 hours. That is, the fasting level is the blood leucine concentration following no food intake for about 12 hours.

BRIEF DESCRIPTION OF THE DRAWINGS

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying drawings, wherein:

Other aspects, embodiments and features will become apparent in the following written detailed description and accompanying drawings.

DETAILED DESCRIPTION OF THE INVENTION

Embodiments of the invention will now be described with reference to the accompanying figures. Unless otherwise specified, the terms used herein are to be interpreted to have a meaning with its usage in this disclosure and/or with its technical and industry usage in any relevant technology area. The terms "including," "comprising," "having," and variations thereof mean "including but not limited to," unless expressly specified otherwise. When used in the appended claims, in original and amended form, the term "comprising" is intended to be inclusive or open-ended and does not exclude any additional, unrecited element, method, step or material. The term "consisting of" excludes any element, step or material other than those specified together with the phrase. It should be understood that the term "about" is used throughout this disclosure and the appended claims to account for ordinary inaccuracy and variability, such as in measurement, testing and the like, in product production, etc.

Without being bound by theory, the inventors believe that a connection exists between plasma leucine, satiety and muscle synthesis. As the skilled artisan would recognize, one of the key roles of protein in the human body is stimulation of skeletal muscle synthesis that supports anabolism. There are other key roles for hormone-related and regulatory proteins in the body for general cellular integrity. These proteins are relatively well-spared from satiety signaling and muscle synthesis and are categorized as "essential." For example, during progression of protein energy malnutrition (PEM), a phenomenon which occurs frequently in undernourished populations, the first phase of PEM is muscle wasting, and the final phase is hormonal function loss accompanied by increased skin fragility (i.e., "cellular integrity loss"). In more well-nourished populations, protein is first used in muscle synthesis/regeneration (muscle grows and degrades, constantly in balance) or as energy stored as fat and consumed daily. For instance, if an individual consumes about 25 grams of protein during a meal, thereby providing just enough protein for basic muscle synthesis, a satiety signal would be sent to the brain to discourage the individual from further eating.

A necessary threshold for plasma leucine appears to exist for stimulating skeletal muscle synthesis in order for other amino acids to be incorporated in muscle protein. Thus, the present inventors theorized that a similar mechanism might apply with respect to the satiety benefit. For example, after a threshold amount of leucine is consumed for basic muscle synthesis, a leucine signal would be sent to the brain to stop eating. Thus, through a concentrated delivery of leucine that achieves a threshold level, a lower absolute amount of protein may be required to induce satiety.

The present inventors have carefully analyzed concentrations of leucine in conjunction with protein to develop a method whereby a more palatable food product can be used to provide the benefit of providing satiety after consumption. A product suitable for use in the method of the invention may advantageously be low in protein, providing options for maximizing taste or flavor.

As used herein, the term satiety is post-ingestive or inter-meal satiety. The skilled person will understand the scope of the term. For example, satiety may be defined as the suppression of further intake of food after eating has ended, and may be assessed in terms of intensity, i.e., the amount of food consumed at a subsequent eating event, and in terms of strength, i.e., the duration of the suppression of hunger (see Blundell J E: *Hunger, Appetite and satiety—constructs in search of identities*. In: Turner M (ed) Nutrition and Lifestyles. Applied Science Publishers, London 1979; 21-42, incorporated herein by reference).

A "food product" as used herein may be in solid or liquid form (e.g., a beverage). It may comprise both solid and liquid portions. In one embodiment, the food product is a cereal product, a granola product, a granola-like product, a nutritional bar, a fortified water, a fruit juice, a fruit smoothie, a dairy smoothie, a dairy beverage, an energy drink, a sachet, a shot, a baked good or a yoghurt. As used herein, a "shot" refers to a volume of about 4 ounces of a liquid product formulation. In one embodiment, the food product is a beverage. A beverage includes, for example, juice beverages (e.g., beverages comprising one or more fruit juices and/or one or more vegetable juices), hydration beverages, frozen beverages, low calorie beverages, etc. In one embodiment, the food product may be a snack product, or a bar, for example, a cold pressed snack bar. It should be understood that snack food products in accordance with this disclosure can have any of numerous different specific formulations or components, so long as the total protein and total leucine is within the ranges disclosed herein.

It is understood that other ingredients may optionally be included in the food product to impart desired qualities to the product, such as texture or flavor. Examples of optional further ingredients include additional flavorings, carbohydrates, fats, vitamins, minerals, sweeteners, sugars, preservatives, food grade acids, food grade bases, colors, salts, fruit pieces, fiber, dairy, antioxidants, masking agents, fruit juices or other fruit products, tastants, flavor enhancers, texture modifiers, and the like but are not limited thereto. Additional and alternative suitable ingredients will be recognized by those skilled in the art given the benefit of this disclosure.

The inventors determined that free form leucine, or leucine that neither forms part of a peptide sequence nor is complexed with a peptide or protein by physical or chemical means, is not very compatible with beverages or bars. For example, free form leucine does not readily incorporate into fluid or liquid mixtures and so processes poorly when preparing food products. However, necessary levels of proteins that supply gram levels of leucine such as those previously reported to induce satiety have generally been at least about 20 grams, and preferably at least about 25 grams. High levels of proteins and/or amino acids, particularly certain amino acids, can be associated with reduced palatability.

The inventors investigated the use of a product previously described by Petersen in U.S. 2011/0233469A1 (referred to herein as "Peterson") for inducing satiety in the method of the present invention. The product of Petersen is produced by combining protein and/or peptides with leucine amino acid by a combination of micronization, admixture, hydration, and co-drying. The resulting product forms a complex between the leucine and the protein and/or peptides with which the leucine is co-processed. Such co-processing forms a product distinct from one having a free form leucine. A product such as that described by Petersen will therefore be referred to herein as a "complexed" leucine product, and products formed by combining peptides and leucine according to the method of Petersen may be referred to as a "leucine-bound peptide" or "leucine peptide composition comprising bound leucine." Products such as these leucine-bound peptides, which provide a more soluble form by which leucine may be delivered, are very effective for producing food products for use in the method of the invention. Leucine-bound peptides made by the method disclosed by Petersen are commercially available as Pepform® Leucine (Glanbia Nutritionals Inc., Monroe, Wis. USA).

Because the inventors have determined that leucine provided in a complex with protein and/or peptides (and more preferably, in the form of a peptide/leucine product such as Pepform® Leucine), provides excellent results for producing a lower-protein product for inducing satiety (as compared to the higher-protein products generally reported in the literature to produce satiety), it is unnecessary to add leucine as a free form amino acid separately to a food product for use in the method of the invention. That is, if the leucine is physically associated with the protein, rather than being provided as an admixture of leucine and protein ("protein" being intended broadly to include peptides), the amount of protein needed to produce the desired satiety effect is reduced. Furthermore, the reduction of the amount of protein, as well as the improved solubility and organoleptic properties provided by a complex formed by leucine and peptides, also result in reduced formulation problems and increased palatability.

The amino acid composition of the leucine-bound peptide product (Pepform® Leucine, Glanbia Nutritionals) is shown below in Table 1. The product, as shown in Table 1, is formulated to provide at least about 40% leucine.

TABLE 1

| Pepform ® Leucine Amino Acid Composition (mg/g Protein) | | | |
|---|---|---|---|
| Tryptophan | 11.14 | Alanine | 27.31 |
| Cystine | 15.07 | Valine | 30.37 |
| Methionine | 10.81 | Isoleucine | 33.64 |
| Aspartic Acid | 67.29 | Leucine | 476.35 |
| Threonine | 42.71 | Tyrosine | 15.73 |
| Serine | 26.32 | Phenylalanine | 15.40 |
| Glutamic Acid/ Glutamine | 108.25 | Lysine | 55.38 |
| Proline | 34.95 | Histidine | 8.96 |
| Glycine | 8.96 | Arginine | 11.36 |

In one embodiment, a leucine peptide composition for use in a product intended for consumption in the method of the invention is one derived from a whey protein isolate (WPI) comprising beta-lactoglobulin, alpha-lactalbumin, and glycomacropeptide (GMP) in approximate ratios of 55%, 20%, and 20%, respectively. Such whey protein isolates can be processed to provide a degree of hydrolysis of between about 10 and about 17 percent to produce peptides for processing to form leucine-bound peptides.

As used herein, "total leucine" refers to the aggregate of all leucine within the food product. In one embodiment, a food product for use in the method of the invention can comprise, per serving size, up to about 3.2 grams of total leucine. In one embodiment, the food product comprises, per serving size, up to about 3.0 grams of total leucine. In one embodiment, the food product comprises, per serving size, up to about 2.8 grams of total leucine. In one embodiment, the food product comprises, per serving size, up to about 2.0 grams of total leucine. In one embodiment, the food product comprises, per serving size, at least about 1.2 grams of total leucine. In one embodiment, the food product comprises, per serving size, at least about 1.5 grams of total leucine. In one embodiment, the food product comprises, per serving size, at least about 2.0 grams of total leucine. In one embodiment, the food product comprises, per serving size, at least about 2.2 grams of total leucine. In one embodiment, the food product comprises, per serving size, at least about 2.5 grams of total leucine. In one embodiment, the food product comprises between about 1.5 to about 3.0 or between about 2.2 to 2.8 grams of total leucine. It should be understood that total leucine refers to the total amount of leucine in one serving size.

A serving size, in one embodiment, is 40-80 grams dry weight or 177-354 mL (or 6-12 fl oz.) liquid. In another embodiment, a serving size may range from about 50 to about 75 grams dry weight. In another embodiment, a serving size may range from about 40 grams_to about 50 grams dry weight. In another embodiment, a serving size may range from about 70 grams to about 80 grams dry weight. In another embodiment, a serving size may range up to about 4 ounces to about 12 ounces (about 118 to about 354 mL) as a liquid. In another embodiment, a serving size may range up to about 8 oz (about 237-240 mL) as a liquid. In one embodiment, the serving size is about 50 g dry weight or about 177 to about 237 mL (about 6 to about 8 fl. oz.) as a liquid.

In one embodiment, a food product for use in the method of the invention comprises, per serving size, protein and leucine, said protein present in an amount of up to about 14.5 grams of total protein. In one embodiment, the food product comprises, per serving size, protein and leucine, said protein present in an amount of up to about 14.0 grams of total protein. In one embodiment, the food product comprises, per serving size, protein and leucine, said protein present in an amount of up to about 13.5 grams of total protein. In one embodiment, the food product comprises, per serving size, at least about 5 grams of total protein. In one embodiment, the food product comprises, per serving size, at least about 8 grams of total protein. In one embodiment, the food product comprises, per serving size, at least 10 grams of total protein. In one embodiment, the food product comprises, per serving size, between about 8 to about 14 grams of total protein, such as about 10 grams total protein. As used herein, "total protein" within a food product as described herein means the aggregate of any and all protein sources within the food product, specifically, the protein from the leucine peptide composition comprising bound leucine within the food product and one or more protein sources within the food product. A protein source suitable for the food product includes, for example, dairy, soy, whey, casein, or more isolated ingredients such as isolates, concentrates, hydrolysates, etc.; including without limitation whey protein isolate, soy protein isolate, non-fat dry milk and the like.

In one embodiment, the food product comprises, per serving size, up to about 14.0 grams of total protein and between about 1.5 to about 3.0 grams of total leucine. In one embodiment, the food product comprises a serving size of about 50 g dry weight or about 177-237 mL (6-8 fl. oz.), and contains about 10 grams total protein and about 2.5 grams total leucine.

The total leucine is provided only by a combination of both total protein and the leucine peptide composition comprising bound leucine. That is, the combination of the leucine peptide composition comprising bound leucine and a protein source within the food product make up the total leucine content of the food product. In one embodiment, at least about 25% of total leucine is provided by the leucine peptide composition comprising bound leucine. In one embodiment, at least about 35% of total leucine is provided by the leucine peptide composition comprising bound leucine. In one embodiment, at least about 50% of total leucine is provided by the leucine peptide composition comprising bound leucine. In one embodiment, up to about 90% of total leucine is provided by the leucine peptide composition comprising bound leucine. In one embodiment, up to about 80% of total leucine is provided by the leucine peptide composition comprising bound leucine. In one embodiment, up to about 75% of total leucine is provided by the leucine peptide composition comprising bound leucine. In one embodiment, between about 25% to about 90%, between about 35% to about 90%, or between about 35% to about 80% of total leucine is provided by the leucine peptide composition comprising bound leucine.

As used herein, "consumer" includes a subject or patient in need of treatment (i.e., the satiety benefit provided by the disclosed method). In general, the consumer or patient in need of treatment ingests a food product comprising per 40-80 grams dry weight or 177-354 mL liquid, protein and leucine, said protein being present in an amount of less than about 15 grams of total protein, and said leucine being present in an amount of between about 1.0 to about 3.5 grams of total leucine, said leucine provided by the total protein and a leucine peptide composition comprising bound leucine. In some embodiments, the food product comprises between about 2.0 to about 3.0 grams of total leucine. In some embodiments, the food product comprises between about 2.0 to about 2.5 grams of total leucine.

Following ingestion, it is believed that the leucine from the food product is digested and passed into the bloodstream of the consumer or patient. This in turn increases satiety. So, satiety is induced by the food product of the present description as a function of blood leucine concentration increasing sufficiently above that of the fasting blood leucine level. However, by using a product comprising a leucine/protein and/or leucine/peptide product, such as the Pepform® product, as an ingredient, the ingredient providing a soluble complex of leucine and protein and/or peptides, the inventors have discovered that it is possible to decrease the amount of protein that must be included in the product in order to achieve a satiety-inducing effect. Previous reports have indicated that protein-induced satiety has resulted from single meals with 25% to 81% of energy from protein in general or from specific proteins (Veldhorst, M. et al. Protein-induced satiety: effects and mechanisms of different proteins. Physiol Behav. 2008 May 23; 94(2):300-7). However, the inventors have discovered that the amount of protein may be reduced, while achieving the same satiety effect (and improving the organoleptic properties of the product for the consumer) by using a complex of leucine and protein (which may be in the form of peptides). Accordingly, one embodiment of the invention is the use of a food product for enhancing satiety by increasing blood levels of leucine relative to a fasting level, said food product comprising, per serving size, protein and leucine, said protein being present in an amount of less than about 15 grams of total protein, and said leucine being present in an amount of between about 1.0 to about 3.5 grams of total leucine, said leucine provided by the total protein and a leucine peptide composition comprising bound leucine. In one embodiment, the method may further comprise the use of the food product as part of an ongoing dietary regime, such as a weight loss regime. In one embodiment, the consumer may be an individual for whom certain medical symptoms would improve, for example, from the imparting of a fullness sensation.

In the method of the invention, it is believed that satiety is induced by an increase in a subject's blood leucine concentration of at least about 2-fold, at least about 3-fold, or at least about 3.5-fold, as compare to fasting leucine levels, by consuming a food product as disclosed herein. That is, a subject's plasma leucine concentration may increase to more than double that of the level in the fasting state, resulting in a satiety response. As used herein, reference to "blood leucine concentration" includes "plasma leucine concentration".

EXAMPLES

The acute effects of consuming protein-nutrition bars enhanced with a leucine peptide (LP) as described herein were assessed on post-prandial appetite and satiety responses in combination with plasma leucine and peptide YY (PYY) concentrations in healthy women. PYY is a peptide found in the gastrointestinal tract, and is known to help reduce appetite.

Utilizing a randomized double-blind crossover design, 40 women (28±7.5 years; BMI: 23.5±2.4 kg/m$^2$) consumed the following isocaloric (180 kcal) pre-loads on three separate visits: control bar [9 g protein; 0 g leucine peptide (LP)] or treatment bars (9 and 11 g protein; 2 or 3 g leucine from LP, respectively). Pre and postprandial appetite (hunger, desire to eat, and prospective food consumption) and satiety (fullness) questionnaires and plasma leucine concentrations were assessed every 30 minutes for 240 minutes. Pre and postprandial plasma PYY concentrations were assessed hourly for 240 min. The results, discussed below, suggest that enhanced leucine content within a lower-protein protein-nutrition bar (2 g LP) may increase ratings of fullness, potentially through the stimulation of PYY, in healthy adults.

Materials and Methods

Nutrition bars for consumption by study participants were made at the Glanbia Nutritionals Collaboration Center pilot facility in Twin Falls, Id. Briefly, an industrial-sized Hobart mixer was used to batch size 6 kg of protein dough for each of the three treatments. First, the PepForm® Leucine powder was dry blended with the other protein powders and fibersol powder (powder mixture "A"). Separately, the powder flavors, maltodextrin, milk minerals (TruCal® D7, milk mineral blend) and artificial sweetener (sucralose) were dry blended to form powder mixture "B". The liquid components (liquid flavors, corn syrup, sorbitol, fiber syrup, melted Cocoa Butter, canola oil, glycerine, soy lecithin and maltitol) were added and mixed well with the beater on medium speed to homogeneity. Powder mixture "B" was added and mixed at low speed for 30 seconds. Powder mixture "A" was then added to the mixing bowl and slowly incorporated for 1-2 minutes until a homogeneous dough was formed. Fruit pieces were added and the bowl surface was scraped to ensure incorporation of all ingredients. Dough was formed into bars of appropriate serving size and coated with melted and tempered coating. Once the coating was set, bars were packaged individually into Mylar foil pouches and sealed, then stored under ambient conditions. Table 2 lists the amounts of the ingredients of the bars for the control product, variant A, and variant B. Amounts listed in Table 2 are for two servings.

TABLE 2

Table 2. Composition of Bars Tested

| INGREDIENTS* | Control C Amount (%) | Variant A Amount (%) | Variant B Amount (%) |
| --- | --- | --- | --- |
| Glanbia Pepform ® Leucine Peptides | | 10.00 | 14.43 |
| Glanbia BarFlex ® 190 WPI | | 12.00 | 11.43 |
| Nutrasol 223 Hydrolyzed Casein | 17.35 | | |
| Blommer Coating, Optisol 1060, Low Sat Fat | 18.00 | 18.00 | 18.00 |
| Light Corn Syrup, Kroger | 6.00 | 6.00 | 6.00 |
| Dried Cherry Pieces, Mariani | 8.00 | 8.00 | 8.00 |
| Maltodextrin Maltrin M100 | 7.52 | 3.20 | 0.44 |
| Sorbitol, 70% Neosorb 70/20 | 6.69 | 6.69 | 6.69 |
| Vitafiber Syrup, IMO, Tapioca Fiber, BioNeutra | 10.00 | 10.00 | 10.00 |
| Canola Oil, Fred Meyer | 4.00 | 4.00 | 3.00 |
| Cocoa Butter, ADM 118302-4P | 2.00 | 2.00 | 2.00 |
| Maltitol MaltiSweet B, Ingredion | 4.00 | 4.00 | 4.00 |
| Glanbia TruCal ® D7 Milk Minerals | 0.88 | 0.55 | 0.45 |
| Fibersol-2, ADM | 5.00 | 5.00 | 5.00 |
| Glycerine, 99.7%, USP, KIC Chemicals | 7.00 | 7.00 | 7.00 |
| Butterbuds Nat Cream + Vanilla | 0.80 | 0.80 | 0.80 |
| Firmenich Nat Vanilla WONF 050005 490T | 0.80 | 0.80 | 0.80 |
| Wixon Nat Bitterless, Pwd 61004194 | 0.20 | 0.20 | 0.20 |
| Comax Nat Protein Masker 3356M16998 | 0.40 | 0.40 | 0.40 |

Forty-eight participants between 18 and 50 years of age with a BMI between 20 to 29.99 kg/m² underwent a medical screening and were selected on the basis of the following inclusion criteria: good health; no use of medications (except for contraceptives or hormone replacement therapy); no history of allergy, sensitivity, or strong dislike towards any of the components of the study products; no use of investigational drug product within the last 30 days; stable weight (within 4 kg) during the last 3 months; no history of a professionally diagnosed eating disorder (e.g., anorexia nervosa, bulimia nervosa, binge eating) or extreme dietary habits (e.g., vegan, Atkins diet, exclusion of major food groups, etc.); score <14 on restraint factor of the Three-Factor Eating Questionnaire (Stunkard, A. J. and S. Messik, *The three-factor eating questionnaire to measure dietary restraint, disinhibition and hunger*. Journal of Psychosomatic Research, 1985. 29(1): p. 71-83, incorporated herein by reference); no use of over-the-counter weight loss drugs and herbal remedies s and dieting programs within two months of visit 1; no history or presence of clinically important renal or gastrointestinal disorders or diabetes mellitus (glucose >126 mg/dL, fingerstick); not pregnant, planning to be pregnant during the study period, or lactating. The study was performed according to Good Clinical Practice Guidelines and approved by the Western International Review Board (Puyallup, Wash., USA). See Table 3 for a summary of the participant characteristics.

TABLE 3

Characteristics of the study participants (n = 40)

| Participant characteristics | Value[1] | P value |
| --- | --- | --- |
| Age (years) | 28 ± 1.2 | 0.62 |
| BMI (kg/m²) | 23.5 ± 0.38 | 0.56 |
| BP systolic | 105 ± 1.6 | 0.51 |
| BP diastolic | 63 ± 1.2 | 0.33 |
| Fasting glucose (mmol/L) | 4.3 ± 0.06 | 0.77 |
| Education (years) | 16 ± 0.46 | 0.22 |

[1]Mean ± SE

Baseline characteristics of study subjects were expressed as mean+standard error (SE) while palatability scores, plasma leucine concentration, all appetite and satiety scores, and PYY responses were expressed as least squares means (LSM)+Standard Error (SE). Differences in the baseline characteristics of study subjects between treatment sequences were evaluated by F-test while differences in the palatability scores were analyzed using a mixed model with treatment as a fixed effect and subject as a random effect. Dependent variables were subscales of appetite and satiety, plasma leucine, and plasma PYY responses. Peak response (Cmax), trough or minimum response (Cmin), apparent time to reach Cmax (Tmax), and/or 240-minute incremental area under concentration-time curve (iAUC) were determined for the study outcomes. iAUC was obtained by linear trapezoidal integration for the area covering the entire assessment window of 240 min adjusted for baseline differences.

The study products (see Table 4 below) were 50-52 g protein-nutrition bars with the functional ingredient PepForm® Leucine (Glanbia® Nutritionals, Inc. (Monroe, Wis.). Bar formulations were aimed at designing a product that delivered increasing amounts of leucine from the peptide carrier while keeping leucine from intact milk protein constant. The leucine from the peptide carrier was 0 g in the control bar (0 g LP) and 2 grams and 3 grams in the treatment bars (2 g LP and 3 g LP, respectively). Varying the protein sources was required to keep the leucine low in the control bar while delivering a constant level of leucine from intact protein across all three bars. The distinct protein sources between bars is not likely a confounder as various distinct protein sources (whey, soy, and egg) below 15 grams do not impact satiety ratings when provided between 5-15 g of total protein. The level of total leucine delivered was determined to correspond to approximately 20-30 g of whey protein isolate (Tang, J. E., et al., *Ingestion of whey hydrolysate, casein, or soy protein isolate: effects on mixed muscle protein synthesis at rest and following resistance exercise in young men*. J. Appl. Physiol. (1985), 2009. 107(3): p. 987-92, incorporated herein by reference). Further, the bars were matched for calories and fat content and were similar in total carbohydrate, dietary fiber, sugar content, and total protein. Although there is a numerical difference in total protein content of 4 grams between the lowest to highest protein levels (0 g LP and 3 g LP treatments, respectively), this represents an inconsequential metabolic difference that likely could not be detected by the subjects.

TABLE 4

Nutritional Content of Nutrition-Protein Bars

|  | 0 g LP | 2 g LP | 3 g LP |
|---|---|---|---|
| Total weight (g) | 50 | 50 | 52 |
| Energy content (kcal) | 180 | 180 | 180 |
| Total protein (g) | 9 | 11 | 13 |
| Total leucine content (g) | 0.77 | 2.77 | 3.77 |
| Leucine from peptide (g) | 0 | 2.0 | 3.0 |
| Leucine from milk protein (g) | 0.77 | 0.77 | 0.77 |
| Total Fat (g) | 6 | 6 | 5 |
| Saturated fat (g) | 2.5 | 2 | 2 |
| Total carbohydrates | 27 | 25 | 24 |
| Sugar (g) | 9 | 9 | 10 |
| Dietary fiber (g) | 6 | 6 | 6 |
| Calcium (%) | 15 | 15 | 15 |
| Palatability (mm)[1] | 48.93 ± 3.60[a] | 46.95 ± 3.64[a] | 42.14 ± 3.67[b] |

[1]Values are LSM ± SE, n = 40.
[a,b]LSM for palatability differ among treatment groups, assessed by fixed effect repeated measures Analysis of Variance (ANOVA) ($p \leq 0.05$).

The trial included a randomized, double-blind, crossover design with one screening visit and three experimental visits. During the experimental visits, the participants arrived at the clinic after an overnight fast of 12 h at 9 a.m. They were randomly provided with the control (0 g LP) or treatment (2 or 3 g LP) protein-nutrition bars and consumed the respective bar within 10 min. Pre and postprandial appetite and satiety, and plasma leucine concentrations were assessed every 30 minutes for 240 minutes. Pre and postprandial plasma PYY concentrations were assessed every hour for 240 minutes. All testing days occurred during the follicular phase of the menstrual cycle. Participants were also encouraged to maintain their normal eating and exercise behavior as well as abstain from alcohol consumption 24 hours prior to each testing day. Compliance was assessed by completing food records after 2 p.m. on the day prior to their visit.

Paper and pencil questionnaires, which assessed perceived sensations of 4 sub scales of appetite (hunger, desire to eat, and prospective food consumption) and satiety (fullness) (Blundell, J. E., et al., Measuring food intake, hunger, satiety and satiation in the laboratory, in Handbook of Assessment Methods for Eating Behaviors and Weight-Related Problems: Measures, Theory and Research, D. B. Allison and M. L. Baskin, Editors. 2009, Sage: Newbury Park, Calif. p. 283-325, incorporated herein by reference) were completed throughout each of the visits at 5, 30, 60, 90, 120, 150, 180, 210, and 240 minutes post study product consumption. In addition, upon completion of the visit day, palatability ("How pleasant have you found the food") to the study products was assessed with questionnaires. Palatability is the response of the consumer or subject to the flavor or acceptability of the food ingested. Both questionnaires contained visual analogue scales incorporating a 100-mm horizontal line rating scale for each response anchored by "not at all" to "extremely". Visual analog scales (VAS) are often used to assess subject appetite sensation through the use of lines with words anchored at each end, typically describing extremes. Subjects then mark the line at that point corresponding to their feelings to those extremes. The distance from the left end of the line to the marked point is then used to quantify the measurement.

On the mornings of visits 2 to 4, a catheter was inserted into the forearm vein for blood sampling and kept patent by saline drip throughout the remainder of the day. The samples were collected in K2-EDTA vacutainers in duplicate. Plasma was separated by centrifugation at 2000 rpm at 4° C. for 20 minutes. After centrifugation, the plasma was transferred into labeled polypropylene tubes. Duplicate samples were frozen at −80° C. for future analysis.

Branched chain amino acid leucine and isoleucine concentrations in these plasma samples were quantified by propyl chloroformate/propanol derivatization, followed by gas chromatography-quadrapole mass spectrometry (GC-MS) (7890A GC, 7000 triple quad MS) (Agilent Technologies, Inc.) analysis in single ion monitoring mode (Dettmer, K., et al., Amino acid analysis in physiological samples by GC-MS with propyl chloroformate derivatization and iTRAQ-LC-MS/MS, in Amino Acid Analysis: Methods and Protocols, Methods in Molecular Biology, M. A. Alterman and P. Hunziker, Editors. 2012, Springer Science+Business Media: Secaucus, N.J., incorporated herein by reference). All sample preparation steps from derivatization to extraction until introduction of the prepared sample into the GC-MS system were performed automatically using Hamilton Microlab® Star™ (Hamilton, UK).

Twenty μL of plasma samples were derivatized with modification for automation, using the Phenomenex® EZ:faast Kit™ (Phenomenex®, Inc.). The derivatized samples were subsequently extracted with isooctane and 2.5 μL of the supernatant was injected into the GC-MS system with helium as the carrier gas. Samples were then separated using rapid temperature gradient programming through a ZB-AAA, 10 m×0.25 μm amino acid analysis GC Column (Phenomenex®, Inc) for a total run time of 9 minutes (Dettmer, K., et al., Amino acid analysis in physiological samples by GC-MS with propyl chloroformate derivatization and iTRAQ-LC-MS/MS, in Amino Acid Analysis: Methods and Protocols, Methods in Molecular Biology, M. A. Alterman and P. Hunziker, Editors. 2012, Springer Science+Business Media: Secaucus, N.J., incorporated herein by reference). Ions at m/z 172 corresponding to leucine and isoleucine and ions at m/z 178 corresponding to isotope labelled leucine and isoleucine (internal standard) were monitored at 2.90 min and 2.99 min retention times for leucine and isoleucine respectively. Concentrations of leucine and isoleucine were calculated based on peak area integration ratios of leucine and isoleucine to their corresponding isotopes labelled to internal standards, using two sets of eight point calibration curves. Accuracy of the analysis was monitored by systematic counter-balancing of test samples with the NIST plasma standards (SRM 1950) and quality control samples. The method was validated for a linear calibration range of 30 μM to 750 μM, with a limit of quantitation of 2.4 μM for both leucine and isoleucine.

PYY was analyzed from previously frozen plasma samples at a subset of timepoints including −5, 60, 120, 180, and 240 minutes. Plasma total PYY was measured using a Sandwich ELISA assay (EZHPYYT66K; Millipore, St. Charles, Mo., USA), SpectraMax M3 Multi-Mode Microplate Reader (Molecular Devices, Sunnyvale, Calif., USA), and Softmax Pro 5.4.1 Microplate Data Acquisition and Analysis Software (Molecular Devices; Sunnyvale, Calif., USA). Although all samples for each subject were assayed, 1 subject had PYY concentrations that were below the limit of detection and were not included within the analyses. Further, the assay protocol indicates that a subject's samples should be run using the same reagents. However, following the completion of the analyses, we found that 15 subjects had samples across multiple assays. Based on protocol, those subjects were remove and a sample size of n=24 is included.

Baseline plasma leucine concentrations (p≥0.4615) and appetite and satiety responses were not statistically different across all four subscales. There was no statistically significant difference between the palatability responses between treatments, however there was a trend towards significance following the 3 g LP compared to 0 and 2 g LP study products (p=0.0491 and p=0.0395, respectively).

To summarize the results: post-prandial fullness iAUC was significantly greater following the consumption of the 2 g versus 0 g LP bar (14.2%; p=0.04); however no significant differences were observed between 3 g LP versus 0 g LP. There were no significant differences in post-prandial hunger iAUC among the treatment groups. There was a dose-dependent increase in $C_{max}$ for plasma leucine compared to 0 g LP (167% and 260% for 2 and 3 g LP, respectively; p<0.0001). $T_{max}$ for plasma leucine for 3 g LP was delayed an average 9.5 min compared to 2 g LP (p<0.0001). This is significantly different between 2 and 3 g LP. The results suggest that enhanced leucine availability within a reduced protein-nutrition bar may increase satiety in humans; however a leucine dose-response was not detected.

Figure 1A:
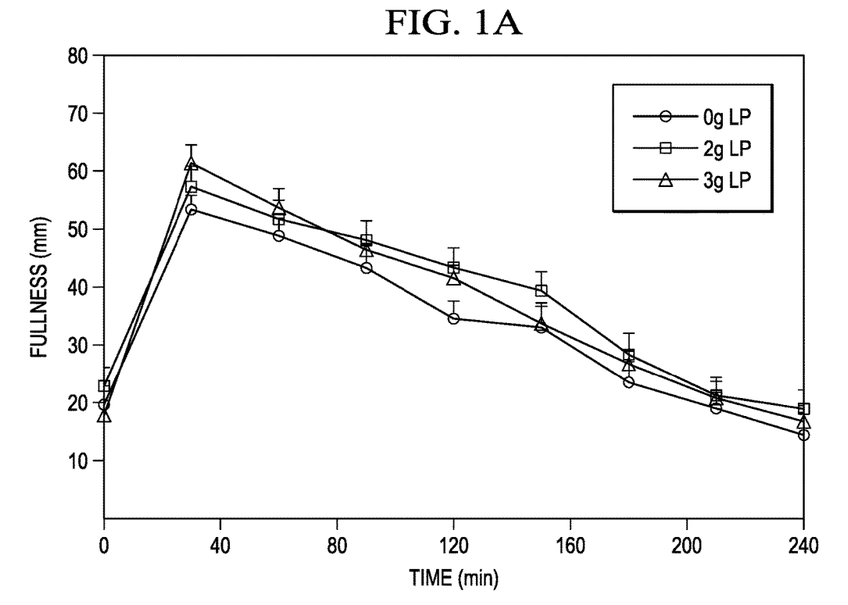
FIG. 1A shows a line graph of the effect of protein-nutrition bars with varying amounts of added leucine on perceived fullness responses over 240 minutes in 40 women.
Figure 1B:
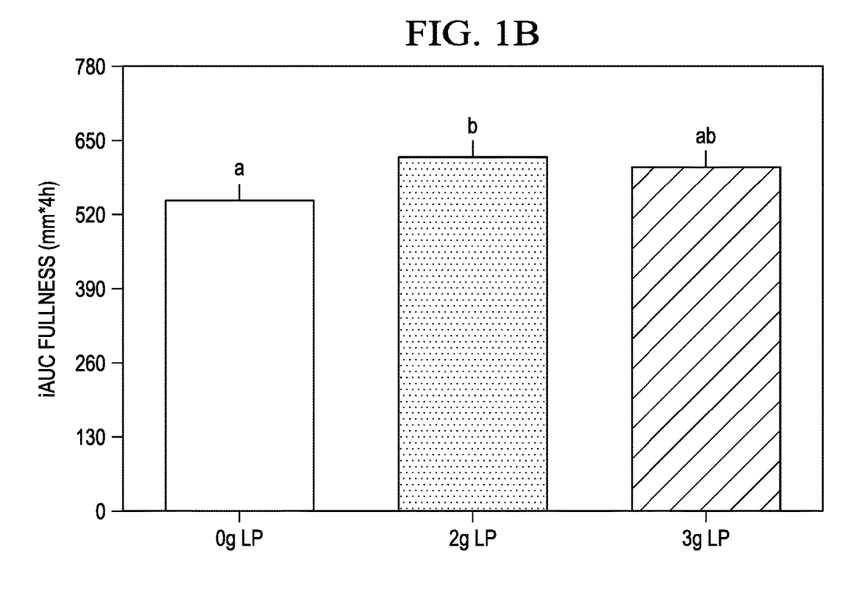
FIG. 1B shows a bar graph of the perceived fullness responses of FIG. 1A using incremental area under concentration-time curve (iAUC) analysis.
Figure 2A:
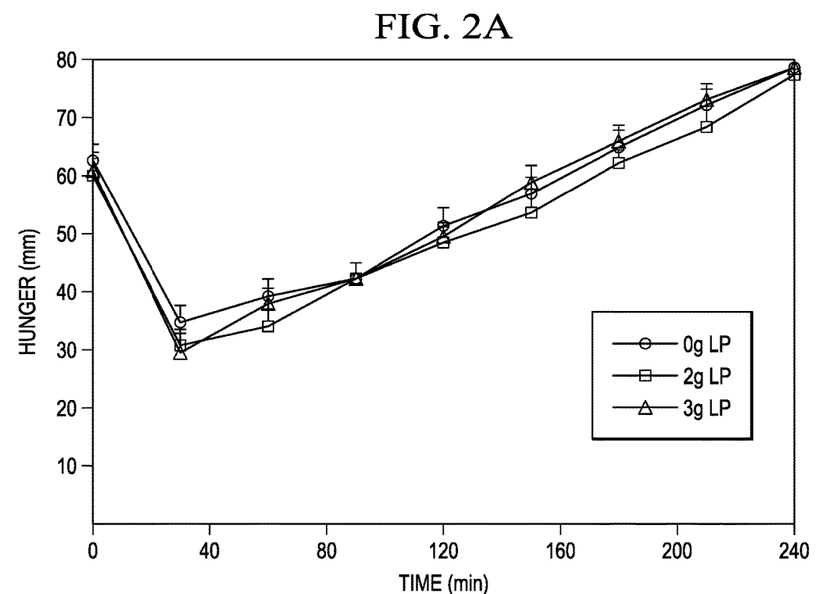
FIG. 2A shows a line graph of the effect of protein-nutrition bars with varying amounts of added leucine on hunger responses over 240 minutes in 40 women.
Figure 2B:
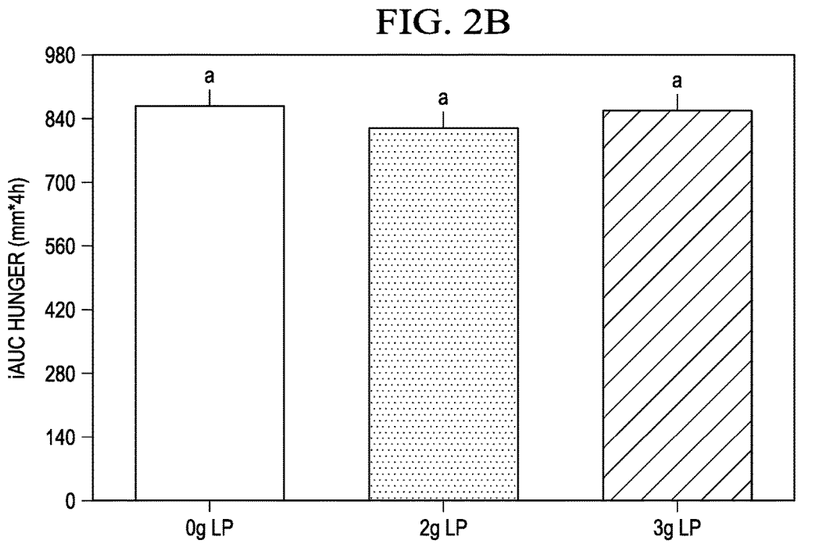
FIG. 2B shows a bar graph of the hunger responses of FIG. 2A using iAUC analysis.

The perceived fullness and hunger responses completed every 30 minutes throughout the 240-minute post-consumption time period are shown in FIGS. 1A and 2A, respectively, whereas the bar graphs in FIGS. 1B and 2B depict the iAUC analyses of their corresponding figures. Values for all figures are expressed as LSM+SE. In the figures, abc denotes the LSM for iAUC differs among treatment groups, assessed by mixed effect ANOVA (p<0.05). With reference to FIGS. 1A and 1B, there was a significant increase in the 240 minute post-prandial perceived fullness iAUC response (of 14.2%) following the 2 g LP compared to 0 g LP (p=0.0359), but not following the 3 g LP (10.7%; p=0.11). Although the fullness iAUC following the 3 g LP was not significantly different from either 0 g nor 2 g LP, $C_{max}$ was 12.2% larger than 0 g LP (p=0.0077). Thus the maximal fullness was significantly greater for 3 g LP. The $C_{max}$ for 2 g LP did not reach significance.

There were no significant differences in post-prandial hunger among the treatment groups as evidenced by the iAUC analysis of the bar graph in FIG. 2B. All three treatments had trough ($C_{min}$) hunger at around 30 minute post-consumption that steadily increased over the remaining assessment time points.

Figure 3A:
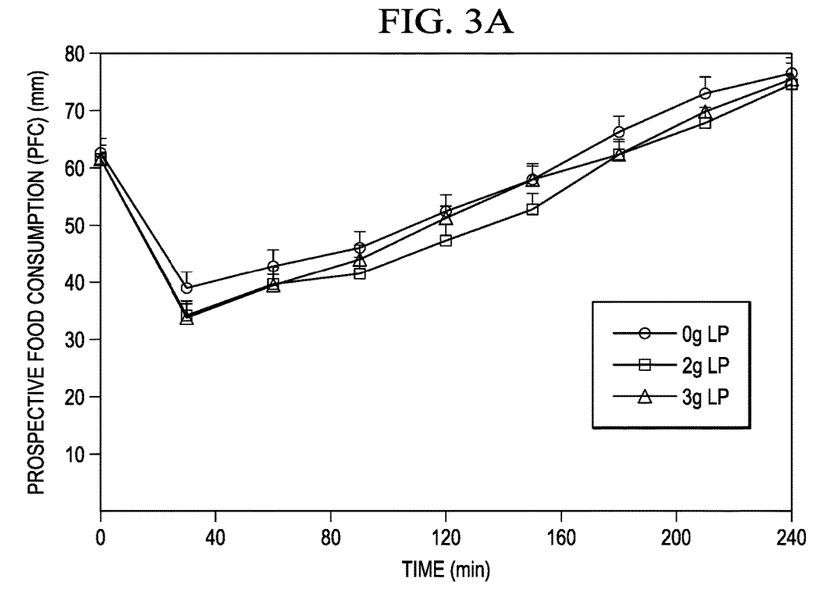
FIG. 3A shows a line graph of the effect of protein-nutrition bars with varying amounts of added leucine on prospective food consumption responses over 240 minutes in 40 women.
Figure 3B:
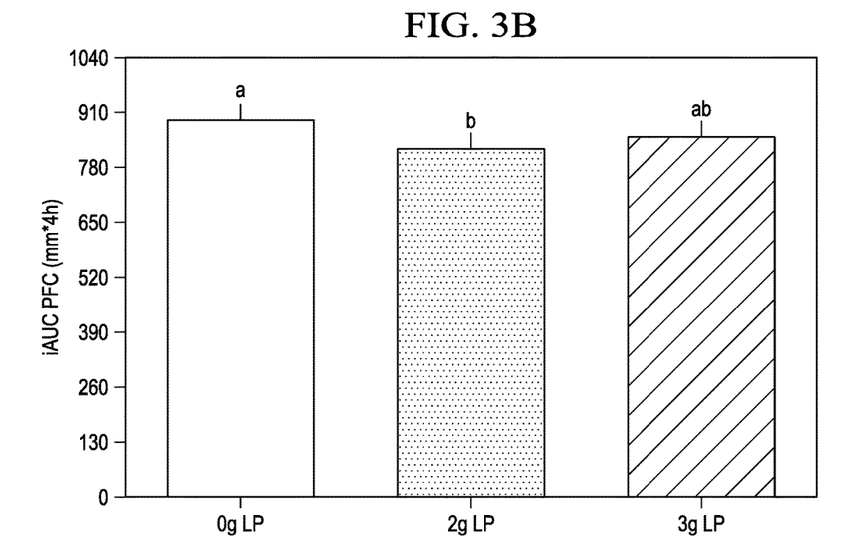
FIG. 3B shows a bar graph of the prospective food consumption of FIG. 3A using iAUC analysis.
Figure 4A:
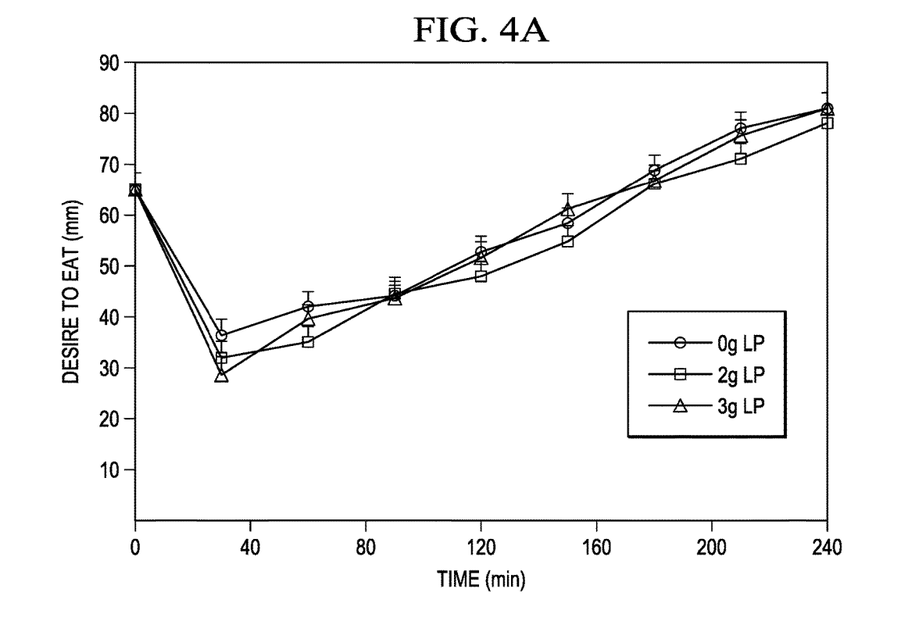
FIG. 4A shows a line graph of the effect of protein-nutrition bars with varying amounts of added leucine on desire to eat responses over 240 minutes in 40 women.
Figure 4B:
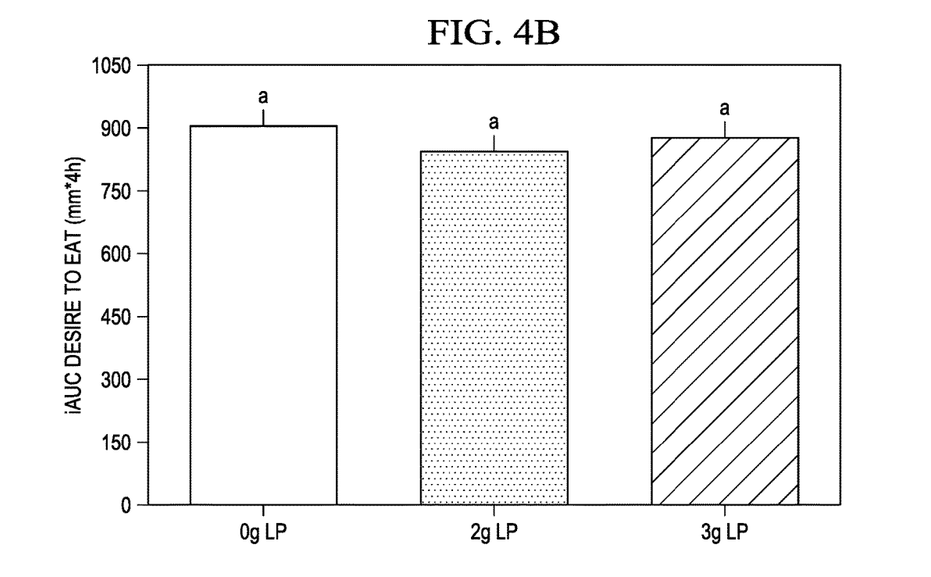
FIG. 4B shows a bar graph of the desire to eat responses of FIG. 4A using iAUC analysis.

The perceived prospective food consumption and desire to eat responses completed every 30 minutes throughout the 240 minute post-consumption are depicted in the line graphs of FIGS. 3A and 4A, respectively, whereas the bar graphs of FIGS. 4A and 4B depict the iAUC analyses of their corresponding figures. As shown in FIGS. 3A and 3B, there was a significant decrease in the 240-minute post-prandial prospective food consumption iAUC following the 2 g LP compared to 0 g LP (7.6%; p=0.0179) but not following the 3 g LP compared to 0 g LP (4.5% p=0.16.). All three treatments had trough ($C_{min}$) prospective food consumption at around 30 minutes post-consumption that steadily increased over the remaining assessment time points.

No significant differences in desire to eat were detected among the treatments as evidenced by the iAUC analysis in the bar graph of FIG. 4B; however, there was a trend towards a difference in iAUC between 2 and 0 g LP (6.5%; p=0.07). All three treatments had trough (Cmin) scores at around 30 min post-consumption that steadily increased over the remaining assessment time points.

Figure 5:
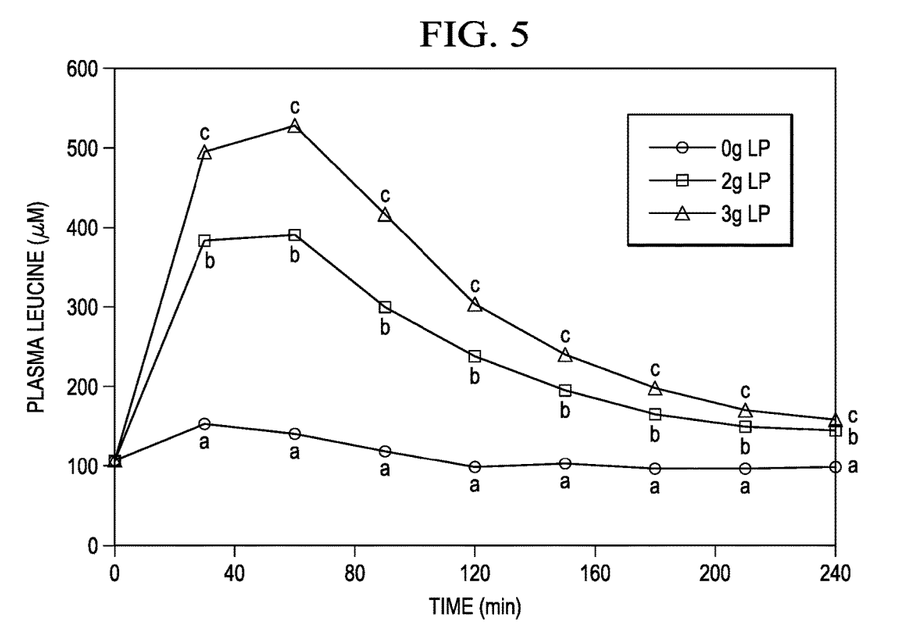
FIG. 5 shows a line graph of plasma leucine response every 30 minutes throughout a 240 minute post-consumption period.

The plasma leucine response is depicted every 30 minute throughout the 240-minute post-consumption period in FIG. 5. As shown in FIG. 5, there was a significant increase in post prandial plasma leucine levels with increased amounts of leucine from the peptide (time by treatment interaction, p<0.001). The $C_{max}$ for 2 and 3 g LP were significantly higher than that of 0 g LP (167% and 260% for 2 and 3 g LP, respectively; p<0.0001), and the $C_{max}$ for 3 g LP was 34.9% higher than that of 2 g LP (p<0.0001). The $T_{max}$ for 3 g LP was delayed on average 9.5 min later than 2 g LP (p<0.0001). Further, the iAUC of 2 and 3 g LP were significantly higher than that of the 0 g LP (p<0.0001) and the iAUC for 3 g LP was significantly larger than 2 g LP (p<0.0001). The pharmacokinetic parameters $C_{max}$, $T_{max}$, and iAUC are shown in Table 5.

TABLE 5

The Dose-Response Effect of Nutrition-Protein Bars with Enhanced Leucine on Pharmacokinetic Parameters over 240 minutes in women

| $C_{max}$ (μM) | | | $T_{max}$ (min) | | | iAUC (μM*4 h) | | |
| --- | --- | --- | --- | --- | --- | --- | --- | --- |
| 0 g LP | 2 g LP | 3 g LP | 0 g LP | 2 g LP | 3 g LP | 0 g LP | 2 g LP | 3 g LP |
| 158 ± 10[a] | 422 ± 10[b] | 569 ± 10[c] | 48 ± 3[a] | 53 ± 3[b] | 62 ± 3[c] | 228 ± 67[a] | 2205 ± 67[b] | 3280 ± 67[c] |

Values are LSM ± SE, n = 40. [abc]LSM for $C_{max}$, $T_{max}$, and iAUC differ among treatment groups, assessed by mixed effect repeated measures ANOVA (p ≤ 0.05).

Figure 6:
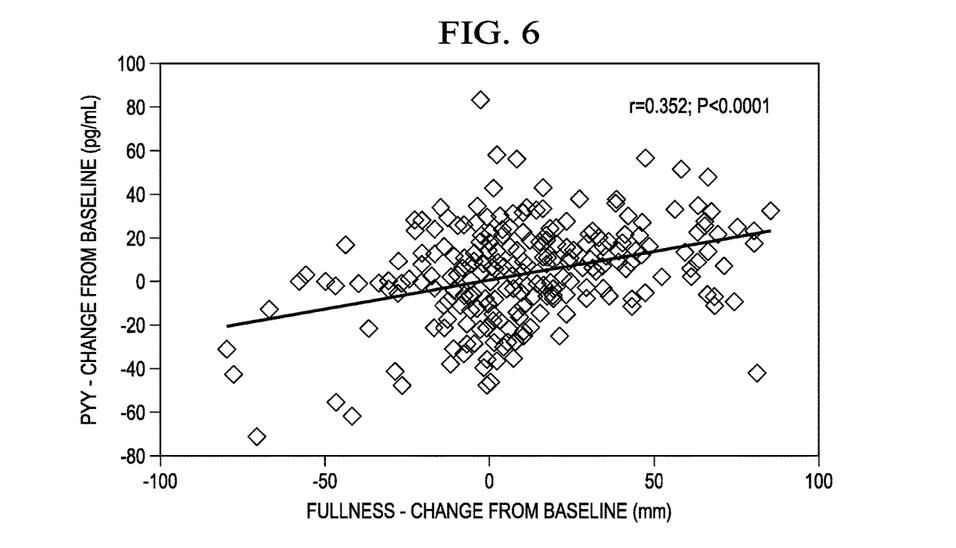
FIG. 6 shows the correlations between post-prandial plasma PYY concentrations and the perceived fullness responses of FIG. 1A.
Figure 7:
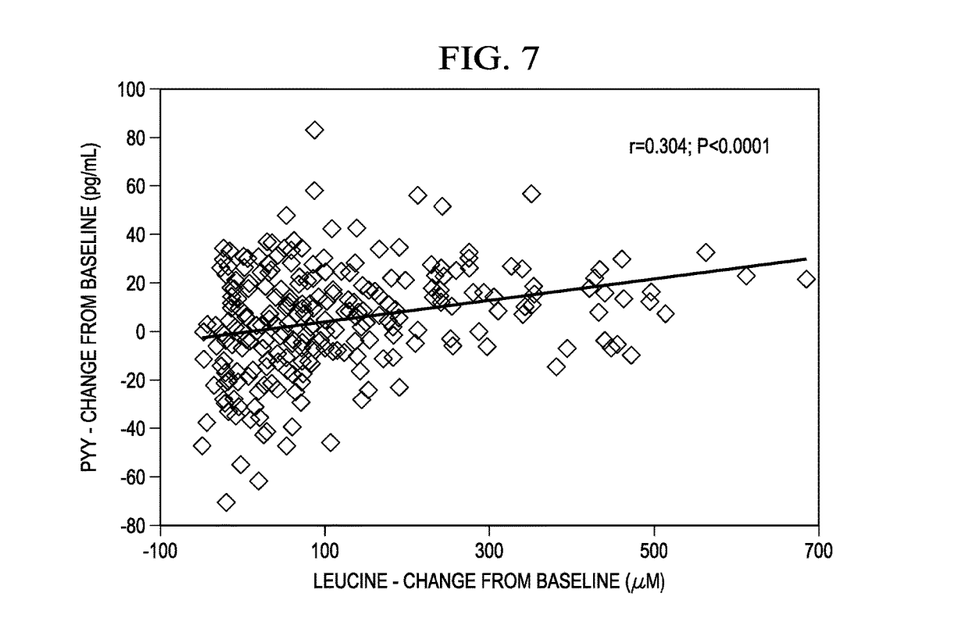
FIG. 7 shows the correlations between post-prandial plasma PYY concentrations and leucine concentrations following intake of protein-nutrition bars with enhanced 0 g, 2 g, and 3 g LP.
Figure 8:
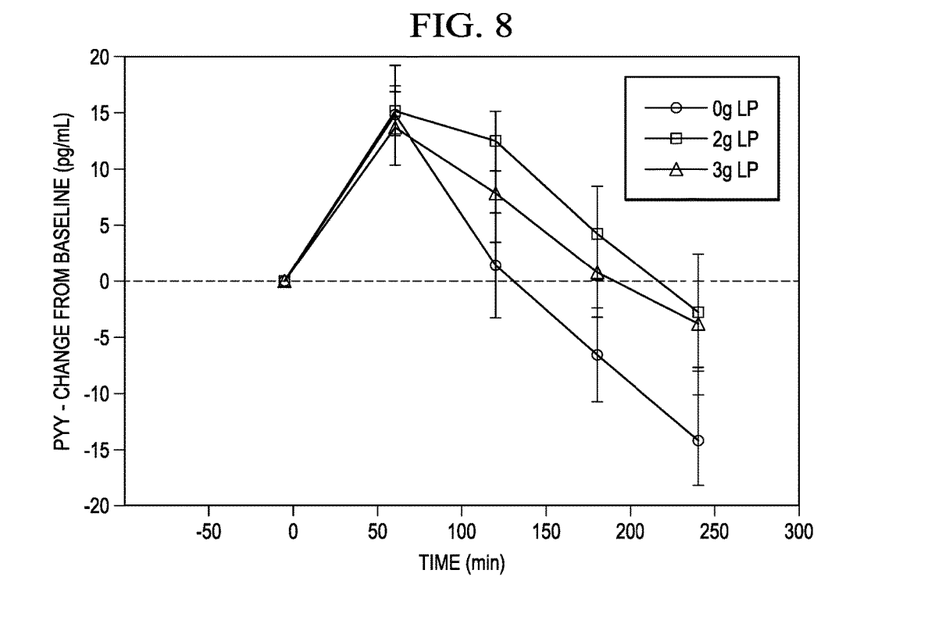
FIG. 8 shows a line graph of the effect of protein-nutrition bars with varying amounts of added leucine on PYY responses over 240 min in 40 women.
Figure 9:
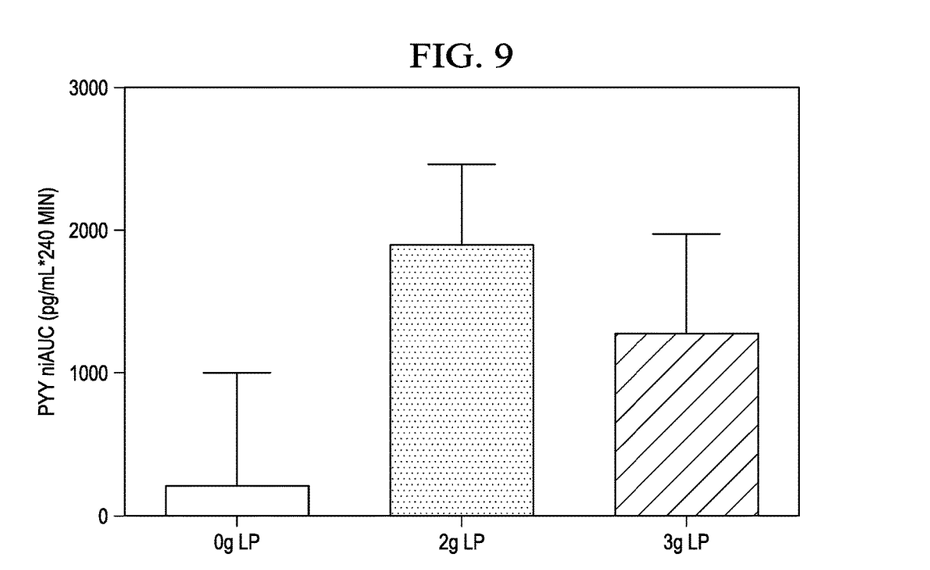
FIG. 9 shows a bar graph of the PYY values of FIG. 8 using iAUC analysis.

Although no main effects of treatment were detected for PYY iAUC, (FIG. 9) exploratory pairwise comparisons revealed a trend for greater PYY iAUC following the 2 g versus the 0 g LP treatment (P=0.064). As shown in FIGS. 6 and 7, Pearson Correlation analyses revealed positive associations between postprandial plasma PYY concentrations, perceived fullness responses, and leucine concentrations.

The above data shows that providing only a 2 g LP dose (versus 3 g) elicits significant effects on select ratings of satiety. It should be noted that the 3 g LP data is provided merely as a comparison example and it contains 3.77 g total leucine. Importantly, the role of plasma leucine kinetics in regulating satiety in humans is unknown. If leucine plays a role it is the peak plasma response, time to reach the peak response, and/or the total iAUC which may drive the satiety response. It is noteworthy that the $T_{max}$ for the 3 g LP dose was on average 9.5 min later than that of the 2 g LP dose. The inventors speculate that the 3 g LP dose may have reached a saturation point from a physiological standpoint.

This data demonstrates a dose-dependent increase in plasma leucine, with the 2 g leucine peptide dose (2205 μM*4 h) effectively exceeding the plasma leucine response previously reported for products containing 40 grams of intact whey protein (see Table 5). In a previous study examining the effect of whey protein on muscle protein synthesis, it was reported that the bioavailability (AUC) of a whey protein beverage containing 2.3 g of leucine was about 3.3 times lower (667 μM*4 h) than the 2 g leucine peptide dose (2205 μM*4 h), shown in the above Table 5. Similarly, in another previous study by the same group, examining the effect of 20 and 40 g whey protein beverage on myofibrillar protein synthesis, it was reported that the bioavailability ($C_{max}$) of leucine in the 40 g dose containing 4 g of leucine was about 1.3 times lower (320 μM) than the 2 g leucine peptide dose (422 μM).

It is well accepted that consumption of high protein meals leads to increases in PYY and perceived satiety compared to normal protein meals. Among the macronutrients, dietary protein elicits the greatest release of PYY. It has been suggested that the amino groups, carboxylic groups and ring structures of amino acids promote PYY release from L-cells located in the ileum and colon. Whether dietary leucine could be driving the protein-mediated release of this satiety hormone is unknown. The present study demonstrated that the greatest increase in PYY concentrations were in response to 2 g LP compared to 0 g LP. This suggests that higher concentrations of leucine (independent of protein) may be uniquely effective in promoting PYY secretion from L-cells. Of note, PYY concentrations also directionally corresponded to the ratings of fullness for the 2 g and 3 g LP, respectively such that the highest leucine dose did not result in the highest PYY response.

The dose response in plasma leucine is not reflected in a consecutive change in satiety response. The above data demonstrates a dose-dependent increase in plasma leucine yet providing only 2 g LP (not 3 g LP) elicits significant effects on perceived satiety. Peak plasma leucine concentrations for the 2 g LP dose exceeds plasma concentrations previously reported with 20 and 40 g of intact whey protein isolate.

While this invention has been particularly shown and described with reference to certain embodiments, it will be understood by those skilled in the art that various changes in form and detail may be made therein without departing from the spirit and scope of the invention. The inventors expect skilled artisans to employ such variations as appropriate, and the inventors intend the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. For example, "and/or" where used herein is to be taken as specific disclosure of each of the two specified features or components with or without the other. For example, "A and/or B" is to be taken as specific disclosure of each of (i) A, (ii) B and (iii) A and B, just as if each is set out individually herein. Further, where values are described as "at most" or "at least", it is understood that any of these values can be independently combined to produce a range.

We claim:

1. A method comprising providing to a consumer a food product comprising, per a serving size of 40-80 grams dry weight or 177-354 mL liquid, protein and leucine, said protein being present in an amount of less than about 13.5 grams of total protein, and said leucine being present in an amount of between about 1.0 to about 3.5 grams of total leucine, said total leucine provided only by a combination of the total protein and a leucine-bound peptide composition, said total protein comprising protein from said leucine-bound peptide composition and one or more protein sources within the food product, said food product inducing satiety in the consumer.

2. The method of claim 1, wherein the step of providing to a consumer the food product forms part of a dietary regime.

3. The method of claim 1 wherein said total leucine is present in an amount of at least about 2 grams.

4. The method of claim 1 wherein the protein is present in an amount of between about 8 to about 14 grams of total protein.

5. The method of claim 1 wherein up to 90% of the total leucine is provided by said leucine-bound peptide composition.

6. The method of claim 1 wherein the food product is selected from the group consisting of a cereal product, a granola product, a granola-like product, a nutritional bar, a fortified water, a fruit juice, a fruit smoothie, a dairy smoothie, a dairy beverage, an energy drink, a shot, a baked good, a yoghurt, and combinations thereof.

7. The method of claim 1 wherein at least about 35% of the total leucine is provided by the leucine-bound peptide.

8. The method of claim 1 wherein at least about 50% of the total leucine is provided by the leucine-bound peptide.

9. The method of claim 1 wherein between about 35% to about 80% of the total leucine is provided by said leucine-bound peptide.

10. The method of claim 1 wherein the food product comprises at least 10 grams of total protein.

11. The method of claim 1 wherein the food product comprises about 10 grams of total protein.

12. The method of claim 1 wherein the food product comprises at least 2.5 grams of total leucine.

13. The method of claim 1 wherein the food product comprises 180 kcal.

14. The method of claim 1 wherein the serving size ranges from about 50 to about 75 grams dry weight.

15. The method of claim 1 wherein the serving size ranges from about 40 to about 50 grams dry weight.

16. The method of claim 1 wherein the serving size ranges from about 70 to about 80 grams dry weight.

17. The method of claim 1 wherein the food product comprises at least 2.2 grams of total leucine.

* * * * *